United States Patent [19]

Lipshitz et al.

[11] Patent Number: 5,391,202

[45] Date of Patent: * Feb. 21, 1995

[54] INTRAOCULAR INSERT FOR IMPLANTATION IN THE HUMAN EYE

[76] Inventors: Isaac Lipshitz, 89A Hanassi Street, 46399 Herzlia; Joseph Gross, 73 160, Moshav Mazor, both of Israel

[ * ] Notice: The portion of the term of this patent subsequent to Oct. 11, 2011 has been disclaimed.

[21] Appl. No.: 188,979

[22] Filed: Jan. 31, 1994

Related U.S. Application Data

[63] Continuation-in-part of Ser. No. 13,387, Feb. 4, 1993.

[51] Int. Cl.⁶ .............................................. A61F 2/16
[52] U.S. Cl. ..................................................... 623/6
[58] Field of Search ................ 623/6; 351/158, 160 R

[56] References Cited

U.S. PATENT DOCUMENTS

| | | | |
|---|---|---|---|
| 4,666,446 | 5/1987 | Koziol et al. | 623/6 |
| 4,955,902 | 9/1990 | Kelman | 623/6 |
| 5,030,231 | 7/1991 | Portney | 623/6 |
| 5,044,743 | 9/1991 | Ting | 623/6 X |
| 5,074,875 | 12/1991 | Donn et al. | 623/6 |
| 5,196,028 | 3/1993 | Portney et al. | 623/6 |
| 5,275,623 | 1/1994 | Sarfarazi | 623/6 |

*Primary Examiner*—Randall L. Green
*Assistant Examiner*—Mary Beth O. Jones
*Attorney, Agent, or Firm*—Benjamin J. Barish

[57] ABSTRACT

An intraocular insert for implantation in the interior of a human eye, characterized in that the insert includes a positive lens to face the anterior side of the eye, and a negative lens in alignment with and spaced behind the positive lens to face the posterior side of the eye.

10 Claims, 2 Drawing Sheets

INTRAOCULAR INSERT FOR IMPLANTATION IN THE HUMAN EYE

RELATED APPLICATION

The present application is a continuation-in-part of our prior application Ser. No. 08/013,387, filed Feb. 4, 1993.

FIELD AND BACKGROUND OF THE INVENTION

The present invention relates to an intraocular insert for implantation in the interior of the human eye to replace the human crystalline lens.

Macular degeneration is a disorder in which the central retinal area (the macula) degenerates, e.g., because of age (age-related macular degeneration, or AMD), diabetic retornopathy, ocular vascular accidents, retinal dystrophies as for example cone dystrophy, central nervous system (CNS) diseases, etc. These disorders in the macular area cause difficulty in vision such that the afflicted person is unable to read without special telescopic or microscopic eyeglasses that create a magnification of the object on the retina. However, when an outside telescope is used, the visual field is very narrowly restricted, and therefore the afflicted person has to move his or her head back and forth to follow the lines being read.

OBJECT AND SUMMARY OF THE INVENTION

An object of the present invention is to provide a novel intraocular insert for implantation in the interior of the human eye particularly for use by persons suffering from macular degeneration diseases.

According to the present invention, there is provided an intraocular insert for implantation in the interior of a human eye, characterized in that the insert includes a positive-power or converging lens carried by the insert to face the anterior side of the eye; and a negative-power or diverging lens carried by the insert in alignment with and spaced behind the converging lens to face the posterior side of the eye.

An intraocular insert constructed in accordance with both the positive lens and negative lens mounted in the interior of the eye increases the visual field that the patient enjoys. Moreover, it obviates the need of using an outside telescope, and therefore the need for the patient to move the head back and forth when scanning lines being read. A further advantage in the above intraocular device to be implanted in the eye, to replace the human crystalline lens, is that it enables the patient also to use outside magnification (e.g., spectacles or contact lenses) in combination with the intraocular insert to achieve higher magnification than possible by using just magnifying spectacles or contact lenses alone.

Further features and advantages of the invention will be apparent from the description below.

DESCRIPTION OF PREFERRED EMBODIMENTS

Figure 1:
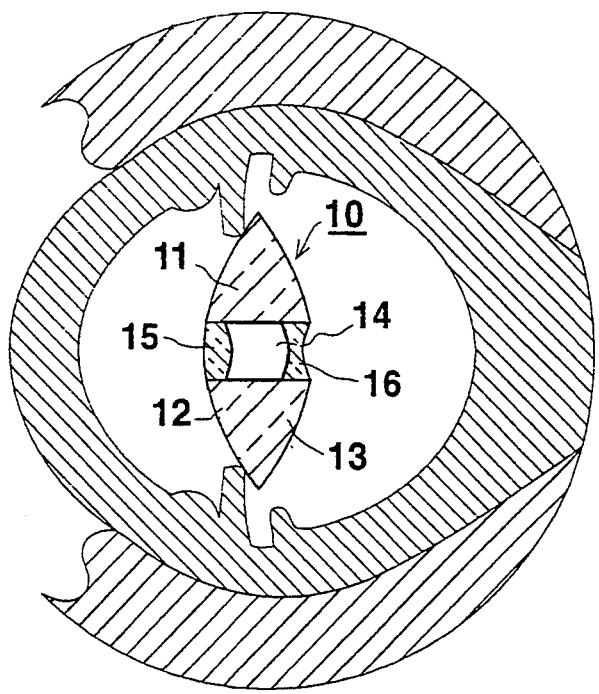
FIG. 1 is a horizontal section of an intraocular insert according to a first embodiment of the invention.

With reference first to FIG. 1, there is illustrated a horizontal section of a human eye, including one form of intraocular insert, generally designated 10, constructed in accordance with the present invention. The means for fixing the insert 10 in the eye are not described herein, as many such means are known for mounting artificial intraocular lenses and can be used for fixing the intraocular insert 10.

The intraocular insert 10 includes a body member 11, of generally convexo-convex or convexo-plano configuration; that is, its front or anterior face 12 facing the anterior side of the human eye is of convex configuration, and similarly its rear or posterior face 13 facing the posterior side of the human eye is of convex (or planar) configuration.

The body member 11 is formed with a central cylindrical bore 14 extending through its anterior face 12 and its posterior face 13.

A positive 15 is fixed within bore 14 at the anterior side of body member 11, and a negative-power or negative 16 is fixed within the bore at the posterior side of the body member. The negative lens 16 is thus aligned with the positive lens 15 but is spaced rearwardly of the positive lens by the cavity defined by bore 14. The two lenses 15 and 16 thus define a Galilean telescopic system commonly used in opera glasses.

Such a telescopic system, when incorporated in an intraocular insert implanted into the human eye in place of the natural crystalline lens, increases the visual field that the patient enjoys, thereby enabling the patient to read fine print without the use of an outside telescope. Thus, the normal eye movements in the reading process are preserved, and the patient does not need to move his or her head from one side of the line to the other in order to read, as generally required when using external telescopic spectacles.

The two lenses 15 and 16 may be made of the same material as presently used for making intraocular lenses, such as transparent plastic (e.g., methyl methacrylate), glass, sapphire or the like. The body member 11 may be of the same transparent rigid material. The cavity 14 between the two lenses 15 and 16 may be filled with a fluid, such as air, a gas, or a suitable liquid such as water.

Figure 2:
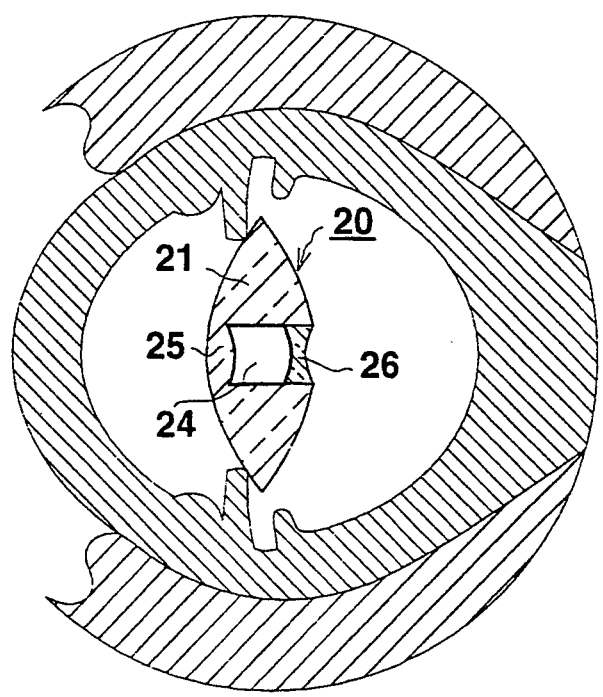
FIG. 2 is a horizontal section of an intraocular insert according to a second embodiment of the invention.

FIG. 2 illustrates an intraocular insert, generally designated 20, similar to insert 10 of FIG. 1, and also including a body member 21 formed with a central cylindrical cavity 24 covered at its front side by a positive lens 25 facing the anterior side of the eye, and at its rear side by a negative lens 26 facing the posterior side of the eye. In FIG. 2, however, the positive lens 25 is integrally formed with the body member 21, whereas the negative lens 26 is formed as a separate element and is fixed, as by an adhesive or a weld, in the rear part of the cylindrical cavity 24 of the body member.

It will be seen that in the constructions of both FIGS. 1 and 2, the outer periphery of the anterior face of the positive lens (15, 25) is substantially flush with the anterior face of the body member 11; and similarly, the outer periphery of the posterior face of the negative lens (16, 26) is substantially flush with the posterior face of the body member 11, 21.

Figure 3:
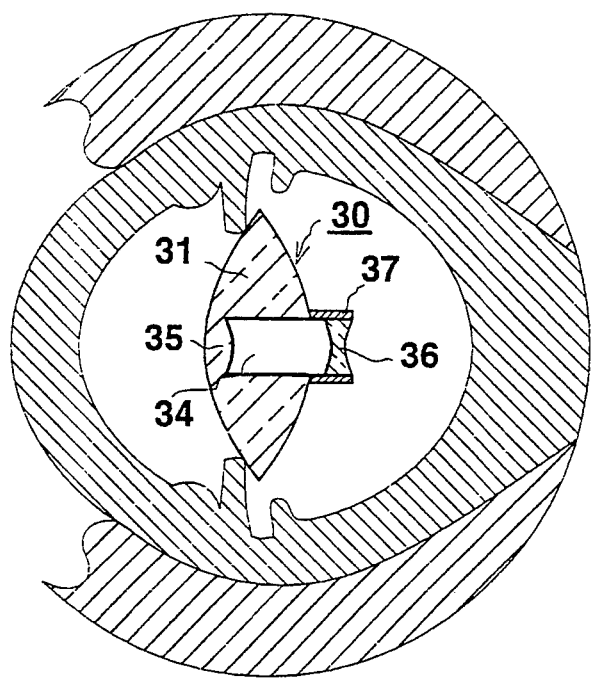
FIG. 3 is a horizontal section of an intraocular insert according to a third embodiment of the invention.

FIG. 3 illustrates an intraocular insert, generally designated 30, also including a body member 31 formed with a central cylindrical bore 34 closed at the anterior end by a positive lens 35 and at the posterior end by a negative lens 36. In this case, however, the negative lens 36 is mounted to the end of a cylindrical lens holder 37 so that it extends rearwardly of the posterior face of the body member 30 and thereby produces a larger space between it and the positive lens 35. Such an arrangement increases the magnification of the intraocular insert.

In all other respects, the intraocular insert 30 illustrated in FIG. 3 is constructed and operates in the same manner as described above with respect to FIGS. 1 and 2.

Figure 4:
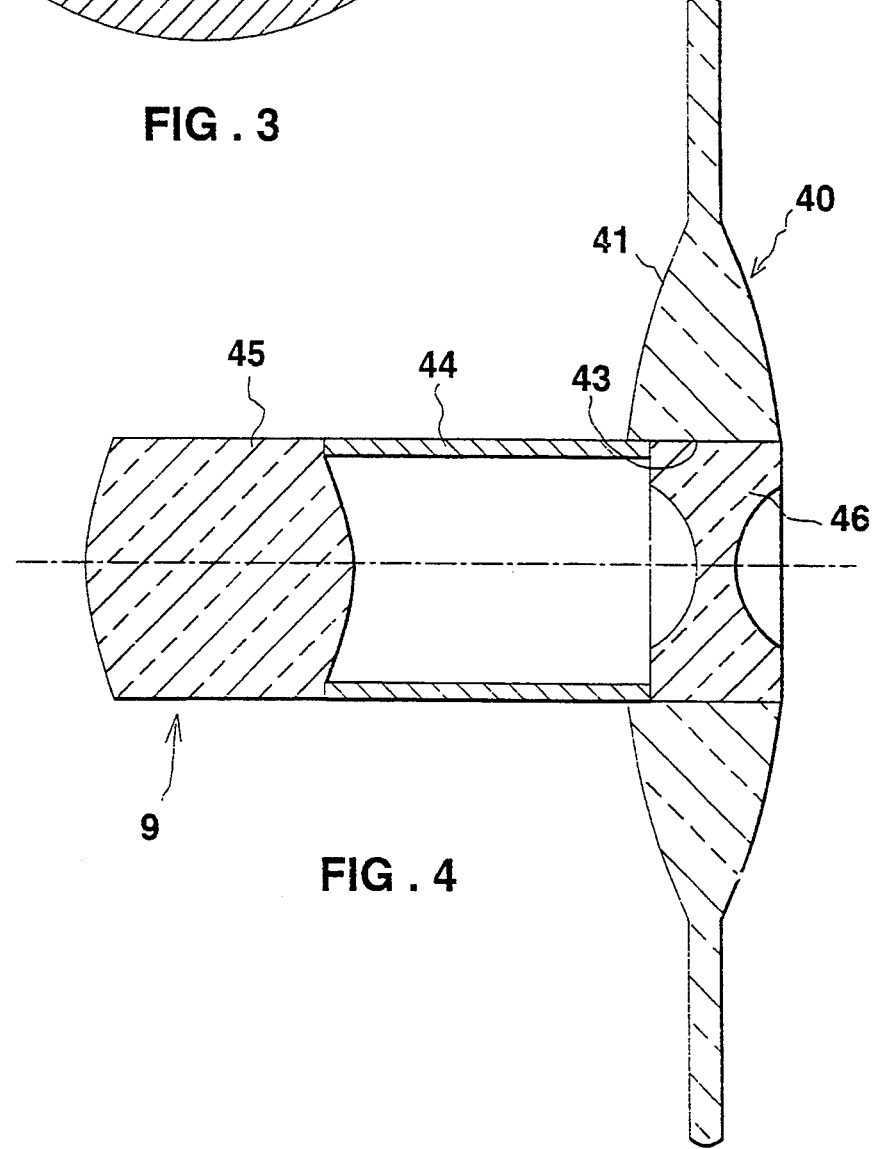
FIG. 4 is a horizontal section of an intraocular insert according to a fourth embodiment of the invention.

FIG. 4 illustrates an intraocular insert, generally designated 40, including a body member 41 in the form of a soft lens formed with a central cavity in the form of a throughgoing bore 43 coaxial with the central axis of the soft lens. A cylindrical lens holder tube 44 is mounted to the anterior side of the soft lens 41 within its bore 43, and carries a positive lens 45 facing the anterior side of the eye. A negative lens 46 is mounted within bore 43 to face the posterior side of the eye. As seen in FIG. 4, the anterior face of the positive lens 45 projects forwardly of the anterior face of the soft lens 41, whereas the negative lens 46 is substantially in coaxial alignment with the soft lens. This produces a relatively large cavity between the two lenses 45, 46, thereby increasing the magnification of the intraocular insert.

The soft lens 41 is preferably made of a silicone, whereas lenses 45 and 46, as well as the cylindrical lens holder 44, are made of transparent glass or plastic. The center cavity of holder 44, between the two lenses 45, 46, may be filled with any suitable fluid, e.g., air, a gas or transparent liquid. In all other respects, the intraocular insert 40 illustrated in FIG. 4 is constructed and operates in the same manner as described above.

In the embodiment of FIG. 4, the body member 41 is preferably a soft lens, but could be a hard lens material, such as of glass, plastic or sapphire. Preferably the cavity defined by the cylindrical lens holder 44 is filled with air, but could be filled with another inert gas or inert liquid.

While it is contemplated that all the elements of the intraocular insert would be implanted as an assembly at one time, it is conceivable that the intraocular insert could include a body member formed with a central cavity implanted in the interior of the human eye, and the lenses attached to the body member during or after its implantation. The intraocular insert could also include more than two lenses, combination lenses, holographic lenses, etc. Many other variations, modifications and applications of the invention will be apparent.

What is claimed is:

1. An intraocular insert for implantation in the interior of a human eye having an anterior face and a posterior face, characterized in that said insert includes:

a positive lens carried by the insert to face the anterior side of the eye;

a negative lens carried by the insert in alignment with and spaced behind said positive lens to face the posterior side of the eye;

and a body member supporting said positive lens and negative lens in spaced relation at the opposite ends of a cavity, in the insert with the outer periphery of a posterior face of the negative lens substantially flush with a posterior face of the body member, and with an anterior face of the positive lens projecting forwardly of an anterior face of the body member.

2. The intraocular insert according to claim 1, wherein said body member includes a soft lens carrying said positive lens and negative lens in alignment with a central axis of said soft lens.

3. The intraocular insert according to claim 2, wherein said positive lens and said negative lens are mounted at the opposite ends of a cylindrical lens holder carried by said soft lens.

4. An intraocular insert for implantation in the interior of a human eye, including a combination of lenses constituting a Galilean telescope to be mounted in the interior of the eye;

said combination of lenses including:

a positive lens to face the anterior side of the eye;

a negative lens in alignment with and spaced behind said positive lens to face the posterior side of the eye;

and a body member supporting said positive lens and negative lens in spaced relation at the opposite ends of a cavity, with the outer periphery of a posterior face of the negative lens substantially flush with a posterior face of the body member, and with an anterior face of the positive lens projecting forwardly of an anterior face of the body member.

5. The intraocular insert according to claim 4, wherein said positive lens and negative lens are separate elements fixed to the body member at opposite ends of said cavity.

6. An intraocular insert for implantation in the interior of a human eye, characterized in that said insert includes a body member of a transparent material formed with a central cavity adapted to receive a positive lens at one end of the cavity and a negative lens at an opposite end of the cavity.

7. The intraocular insert according to claim 6, wherein said central cavity is a throughgoing bore.

8. The intraocular insert according to claim 6, wherein said central cavity is integrally formed at one end with one of said lenses.

9. The intraocular insert according to claim 6, wherein said body member is a hard lens.

10. The intraocular insert according to claim 6, wherein said body member is a soft lens.

* * * * *